(12) United States Patent
Flesch et al.

(10) Patent No.: US 6,733,457 B2
(45) Date of Patent: May 11, 2004

(54) MOTORIZED MULTIPLANE TRANSDUCER TIP APPARATUS WITH TRANSDUCER LOCKING

(75) Inventors: Aimé Flesch, Andrésy (FR); An Nguyen-Dinh, Valleres (FR)

(73) Assignee: Vermon, Tours Cedex (FR)

( * ) Notice: Subject to any disclaimer, the term of this patent is extended or adjusted under 35 U.S.C. 154(b) by 205 days.

(21) Appl. No.: 10/166,168

(22) Filed: Jun. 11, 2002

(65) Prior Publication Data

US 2003/0229287 A1 Dec. 11, 2003

(51) Int. Cl.⁷ .................................................. A61B 8/14
(52) U.S. Cl. ....................................................... 600/459
(58) Field of Search ................................. 600/437, 438, 600/439, 407, 415, 424, 429, 442, 443, 444, 445, 446, 447, 451, 459, 461–472; 128/898, 916; 73/620–630; 367/7, 11, 130, 138; 606/32; 604/11, 19; 607/1, 2; 601/2, 3

(56) References Cited

U.S. PATENT DOCUMENTS

| 4,543,960 A | 10/1985 | Harui et al. |
| 4,802,487 A | * 2/1989 | Martin et al. ................ 600/463 |
| 4,841,977 A | * 6/1989 | Griffith et al. ............... 600/439 |
| 5,176,142 A | 1/1993 | Mason |
| 5,181,514 A | 1/1993 | Solomon et al. |
| 5,445,154 A | 8/1995 | Larson et al. |
| 5,456,256 A | 10/1995 | Schneider et al. |

FOREIGN PATENT DOCUMENTS

| WO | WO 91/19458 | 12/1991 |

\* cited by examiner

Primary Examiner—Ali M. Imam
(74) Attorney, Agent, or Firm—Larson & Taylor, PLC

(57) ABSTRACT

An ultrasonic endoscopic probe tip device which provides signals to an imaging system for transesophageal diagnosis includes a removable housing adapted to be attached to the distal end of an endoscope. A rotatable, ball-bearing-mounted phased array transducer within the housing is rotatable around its acoustic propagation axis through multiple turns. The transducer is driven by an immersed micro-motorized drive. A torque limiting gearbox couples the drive to the transducer. A position encoder provides the imaging system with transducer position information over a 360° range. An automatic transducer position locking/unlocking system is used to lock the transducer in a selected rotational position.

13 Claims, 2 Drawing Sheets

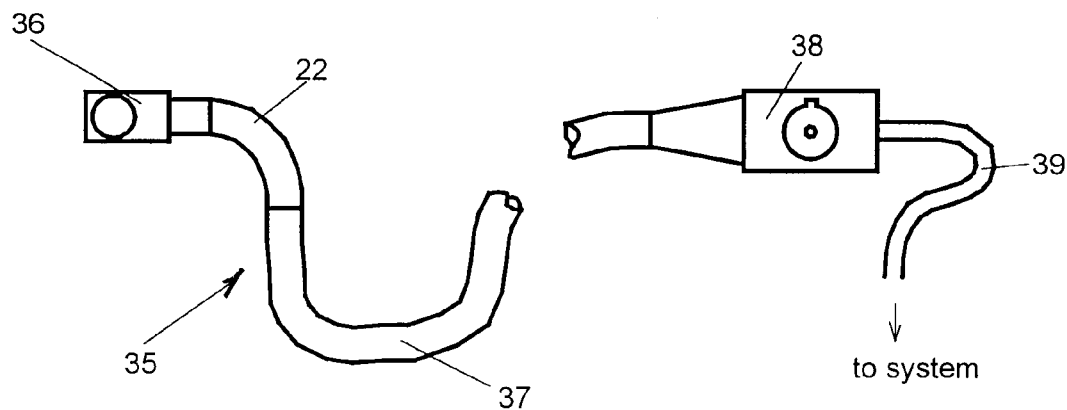
Figure 1
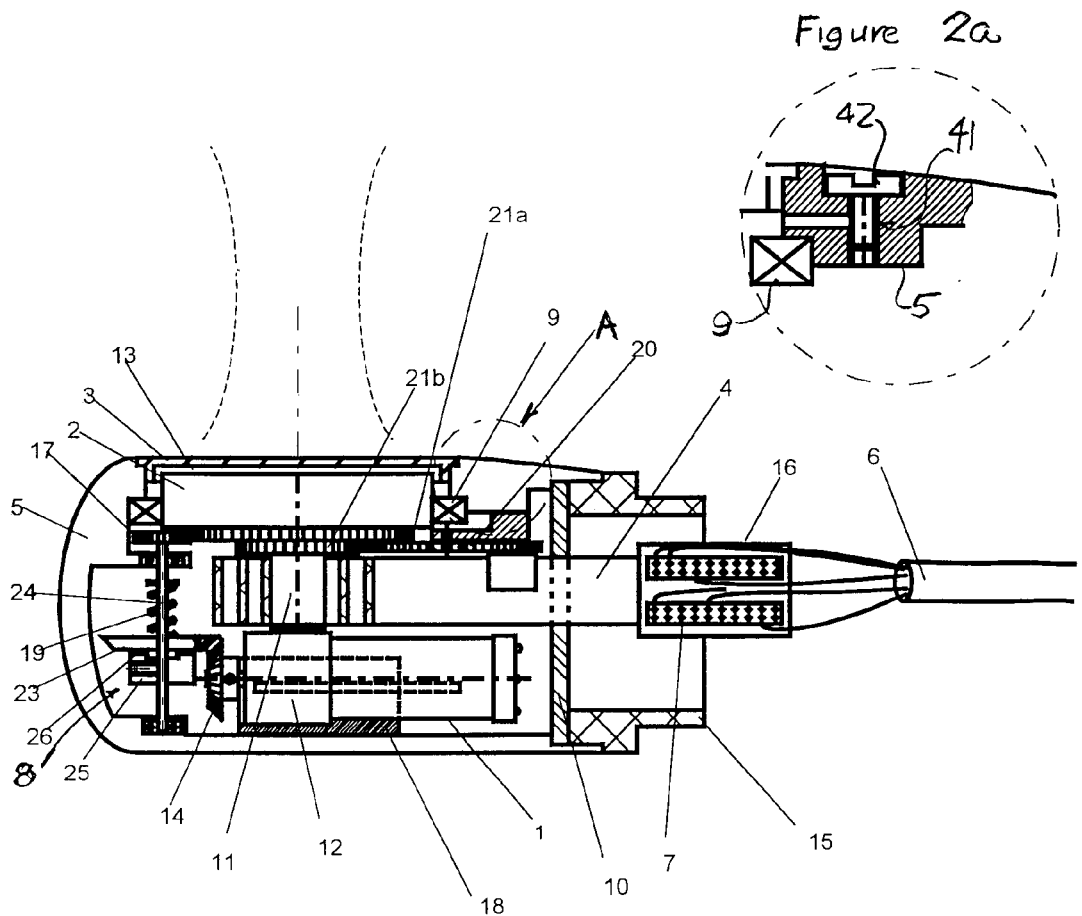
Figure 2a
Figure 2

MOTORIZED MULTIPLANE TRANSDUCER TIP APPARATUS WITH TRANSDUCER LOCKING

BACKGROUND OF THE INVENTION

1. Field of the Invention

The present invention relates to ultrasonic probes and, more particularly, to motorized transducer ultrasonic probes for trans-esophageal imaging.

2. Background of the Invention

Commercial transesophageal (TE) ultrasonic probes are typically provided with either a biplane or multiplane phased array transducer mounted at the distal tip of the endoscope. The biplane device is based on the integration of two phased array transducers which have the acoustic azimuth planes thereof oriented perpendicular to each other, while the multiplane device uses a single phased array transducer which is rotated around the Z-axis thereof (i.e., in the wave propagation direction). The flexibility and ease of use thereof make multiplane transducer probe the preferred instrument for use in transesophageal examinations in spite of the relatively high cost of such apparatus.

The terms scanhead, transducer tip housing, distal housing and distal tip are all sometimes used for designating the sensor compartment or section wherein the ultrasonic transducer is located. In TE applications, the dimension of the scanhead must be relatively small and, in general, must not exceed 20–25 mm in length and 12–14 mm in diameter, in order to avoid patient discomfort.

Currently, the fabrication of multiplane or 3D phased array TE probes is a highly complicated operation because of the complex components needed to provide precise rotation of transducer. Further, in order to keep the size of the scanhead of the TE device small enough to enable easy insertion thereof into the esophagus, the rotary drive means for the transducing device is typically remotely located in the handle of the endoscope in that more space is available there.

Generally speaking, the transducer rotary drive means can be an electric motor or a manually actuated device, respectively associated with a flexible drive shaft or cables. In case of motor drive device, the rotary drive shaft is provided in an elongated anti-torsion rod or tube and extends through the flexible tubular portion of the endoscope to connect to the transducer. In the handle of endoscope are also provided all of the controls for steering and positioning the scanhead. Transmission of the controls exerted from the handle to the scanhead of the endoscope is typically effected through a set of cables secured to the two respective parts. A bendable coupler or connection is provided between the scanhead and the flexible tubular portion of the endoscope to effect this operation.

There are numerous documents and literature references disclosing manufacturing and construction techniques for ultrasonic TE imaging endoscopic probes. These documents include, for example, U.S. Pat. No. 4,543,960 to Harui et al wherein a rotating ultrasound transducer is mounted in the scanhead of an endoscope. This patent discloses a transducer platform on which a multi-element transducer is assembled and fastened to a pulley. A pair of cables, extending from the endoscope handle controls, is then attached to this pulley to provide rotational movement of the transducer. The transducer electric wire bundle is complemented by a flexible printed circuit board (PCB). Although the transducer cable drive system as described in the Harui patent is relatively simple to build, the system must be maintained in constant cable tension in order to provide accurate rotation of transducer. Further, in a bendable endoscope, such cable drive device is fragile and inaccurate. Otherwise, no encoder is provided on the transducer, and the acoustic coupling method between transducer and the medium of interest is not addressed in the patent.

In U.S. Pat. No. 5,181,514 to Solomon et al and U.S. Pat. No. 5,176,142 to Mason, multiplane TE ultrasonic probes are disclosed which are an improvement over the probes of the Harui patent. An interconnect wire bundle management arrangement is disclosed, with a flexible PCB being located in two separated volumes provided in the endoscope transducer tip so that during rotation of transducer, the flexible PCB is transferred from one volume to the other via a take-up mechanism. A drive motor and encoder are mounted in the handle of endoscope. Rotational movement is transmitted to the scanhead via a flexible drive shaft. A gear assembly is provided in the vicinity of the transducer which mates with the drive shaft for the transducer. The Solomon et al patent also mentions the possibility of assembling both the motor and encoder in the transducer tip although no detailed description is provided in the patent and the mechanism described is explicitly designed for the endoscope handle. Further, the take-up mechanism for the flexible transducer PCB described therein results in a significant increase in the occupied volume in the tip housing that precludes or inhibits any possibility of motor integration in this part of the device. The position encoder, which includes a potentiometer as described in the patent, is of a construction incompatible with use thereof in a small TE probe tip volume. In addition, although a gearbox is provided to reduce the torque resistance transferred to the drive shaft, a variation in the friction force encountered by the transducer will produce torsional bending of the shaft, thereby leading to oscillations in the rotational speed of the transducer as well as significant motor current consumption, with the attendant risk of electrical noise appearing in the images produced.

In PCT application WO91/19458 to Ingebrigsten, a TE ultrasonic probe is disclosed which includes an endoscope distal housing comprising a rotatable shaft extending longitudinally along the housing, a motor for rotating the shaft and a multi-element ultrasonic transducer array connected to the shaft. The array is electrically connected by a first flexible PCB that extends, in S-like undulating manner, to a second flexible PCB which extends outwardly of the tip. The direct coupling between the transducer and motor eliminates the use of a flexible drive shaft; however, the output of the flexible transducer PCB exhibits a non-linear resistance force during operation resulting in an unreliable interconnection. Further, the technique disclosed of using a flexible PCB output prevents rotation of the transducer through a full turn. Finally, no rotation along the propagation axis of transducer is disclosed, thus dramatically limiting use of the device in TE modalities.

U.S. Pat. No. 5,445,154 to Larson et al discloses a multiplane ultrasonic probe wherein a cupped member is provided that receives a multi-element transducer array. The cupped member is mounted in a base unit via a low friction dynamic seal joint. The cupped member is attached to a drive gear which is engaged with a drive train. Rotation of the cupped member is produced by a ratchet gear driven by a pair of solenoids disposed in the handle of endoscope. A pulling or pushing action is transmitted to pawls by control cables. This method of driving the transducer in rotation is similar to those disclosed in the Harui patent and suffers from the same drawbacks described above. Further. The ratchet gear arrangement results in step by step rotation of the transducer and thus inhibits any 3D, on the fly acquisition. With regard to the dynamic seal mount, this requires the use of a large diameter seal and results in increased friction.

U.S. Pat. No. 5,456,256 to Schneider et al discloses an ultrasonic imaging system and apparatus wherein a sealing method is provided for separating the chamber for the liquid coupling from the outside. The transducer is typically a single element device and is mounted at the extremity of an oscillating arm. An oscillating platform is driven by a first motor which is directly coupled to the rotatable axis of the transducer arm. A second linear motorized drive is provided in the scanning plane in a manner such as to move the scanning line along the scanning surface. The transducer and arm are entirely immersed in the coupling liquid and the coupling bath is maintained in place by the use of a first oscillating sealed reservoir that surrounds the transducer area. Because the motor has to be isolated from the liquid, a second flexible seal is provided on the rotational axis of device. The second seal is designed such that a certain amplitude of alternate rotation of the axis is tolerated. This method is designed for scanning applications wherein dimensional constraint is not a concern. Moreover, moving such an arm in liquid will produce high movement resistance which is conducive to bubble formation in the liquid, resultant non-linear movement of transducer, or a significant variation in motor current when operating at high oscillating rates.

When considering the complexity of prior art TE ultrasound probes, and particularly those featuring a multiplane capability, it is evident that the prior art constructions of distal ultrasound transducer tips for endoscopic use suffer important disadvantages and, in general, are such as to make the instruments so specialized and intricate as to inhibit improvement on the quality and reliability thereof. Moreover, the annual maintenance of such prior art probe devices can cost up to one third of the purchase price, and despite the high quality of fabrication associated with such devices, the severe conditions to which the devices are subjected in medical applications has required that TE probes be mechanically inspected at least yearly in order to comply with current safety and performance specifications. There is, therefore, an obvious need for a TE ultrasonic diagnostic probe which has significantly improved reliability while, at the same time, decreasing the current purchase price and maintenance cost of such probes.

SUMMARY OF THE INVENTION

In accordance with a first aspect of this invention, a modular ultrasound endoscope is provided having three sections, viz., a handle, a flexible elongated tubular portion or tube and a transducer tip. More particularly, the transducer tip comprises an integrated plug-in module that can be from, and plugged into, the endoscope tube by a user after having received minimal instruction. This capability dramatically reduces the cost of the device and enables the use of several transducer tips with a single endoscope.

A second aspect of the present invention particularly addresses the positional accuracy of the transducer when operating in the scanhead. A separate locking/unlocking system is provided for the transducer and is connected to the motor power supply so as to be automatically synchronized with the rotation and stopping of the motor. Integration of the locking/unlocking system into the scanhead volume allows the use of a conventional small size electrical motor for driving the transducer without the occurrence of noise.

Further features and advantages of the present invention will be set forth in, or apparent from, the detailed description of preferred embodiments thereof which follows.

BRIEF DESCRIPTION OF THE DRAWINGS

FIG. 1 is a schematic representation of the basic components of an ultrasonic endoscopic probe device;

FIG. 2 is a cross sectional view of a probe tip in accordance with a preferred embodiment of the invention;

FIG. 2a is a detail of a portion of the probe tip of FIG. 2, indicated at A;

DESCRIPTION OF THE PREFERRED EMBODIMENTS

Figure 3A:
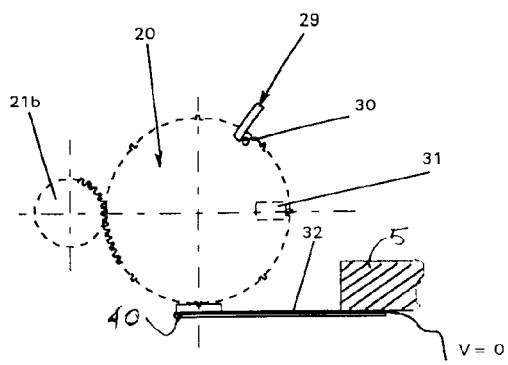
FIGS. 3a and 3b, FIGS. 4a and 4b and FIGS. 5a and 5b are top plan views of transducer locking/unlocking systems in accordance with three different preferred embodiments of the invention, each pair of figures showing the operative and inoperative states of the respective locking/unlocking system.

Referring to FIG. 1, there are shown the basic units or components of a transesophageal ultrasonic endoscopic probe constructed in accordance with a preferred embodiment of the invention. It will be understood that while the invention has been described above and is described below relative to a transesophageal ultrasonic endoscopic probe, the invention is not limited to this application and can be easily designed for other endoscopic modalities such as industrial controls, inspection systems and the like. In FIG. 1, an endoscope or ultrasonic endoscopic probe, generally denoted 35, includes a transducer tip 36 connected by flexible or bendable coupler 22, preferably formed from an assembly of rings (not shown) as described in U.S. Pat. No. 5,681,263 to Flesch, to an elongated tube 37. Tube 37 can be flexible or rigid and is connected to an endoscope handle 38 which contain steering controllers (not shown) for the transducer tip 36. A cable 39 connects the handle 38 to the imaging system (not shown) for the probe 35. It will be appreciated that the probe 35, as shown in FIG. 1, is of a conventional construction typical of such devices and is presented here to place the description which follows in context.

Referring to FIG. 2, a transducer tip or scanhead is shown which includes a housing 5 having an acoustic window 3 mounted in a wall thereto located near the distal end of the scanhead and positioned in the acoustic path of a transducer 2. Housing 5 is preferably made of a medical plastic such as PEEK, Ultem, Surlyn or an equivalent. In general, the material for housing 5 must be medically compatible with, and be able to withstand, all of the disinfecting solutions currently used. The housing 5 is further sealed at its proximal side or end by a membrane 10 which is maintained in contact against the housing 5 by a threaded ring 15. An optional O-ring seal (not shown) can be disposed at the interface between the membrane 10 and the housing 5 so as to improve fluid tightness. Housing 5 contains, and has sealed therein, a volume of acoustic coupling liquid 13, this volume being delimited by the internal surface of housing 5. As described below, the housing 5 also houses transducing and motorization components that are immersed in the coupling liquid bath 13.

Under the window 3, sealed to housing 5, is mounted the phased array transducer 2 which was mentioned above and which is preferably circular shaped to minimize any liquid turbulence in coupling liquid 13 caused by the rotation of the transducer 2.

Transducer 2 is mounted in a ball bearing 9 which is, in turn, secured to a receptacle therefor provided in the housing 5 as can be best seen in FIG. 2a. It is important to note that ball bearing 9 can be replaced by a dry bearing, or an equivalent device with no significant impact on the operating characteristics of the probe.

Transducer 2 has a front surface which faces the window 3 through which acoustic energy passes. Optionally, focusing silicon lens (not shown) can also be provided if geometrical focusing is desired.

At the bottom face of the transducer 2, gears or gear wheels 21a and 21b are provided which are secured to the transducer 2 (i.e., to the transducer housing) and which are preferably made of a plastic material. The gears 21a and 21b are respectively connected to driving and encoding gear systems described below.

At the central bottom side of the transducer 2, a cylindrical shaft or axle II is disposed. An output flexible printed circuit board (PCB) 4 is connected to the transducer electrodes and wraps around the cylindrical shaft 11 so as to maintain the volume occupied by the wrapped PCB 4 compatible with the available volume or space. PCB 4 terminates at an interconnection unit or connector 16. The PCB 4 may be one of several different types such as single layer, grounded single layer, double layer or grounded double layer, depending on the transducer specifications. Because the signals transmitted through flexible circuits of PCB 4 are subject to electromagnetic interference, these circuits are designed to be as short as possible and are connected to a suitable transmission line such as coaxial cable 6. Preferably, referring again to FIG. 1, the interconnection unit 16 is provided at the immediate junction area located between the transducer tip 36 and the bendable endoscope coupler 32 shown in FIG. 1. Such a location or disposition makes the interconnection unit 16 free of the bending constraints which are inherently exerted on conventional endoscopic devices.

With regard to the management of the flexible PCB 4 inside of the transducer tip housing 5, the amount of coiling of the flexible circuit of PCB 4 on cylindrical axle 11 is preferably determined based on the number of rotations that transducer 2 has to undergo. In general, at the maximum rotational position of the transducer 2, the flexible circuits PCB 4 should be not in frictional contact with each other in order to prevent wear, and to, therefore, avoid loss of contact or short circuiting of the PCB circuits. For instance, 3D imaging cardiac applications will require the transducer 2 to rotate through at least a complete rotation per cardiac cycle so the length of flex circuit should be determined accordingly.

At the bottom side of the housing 5 as viewed in FIG. 2, a support 18 for a motor 1 is provided. Support 18 enables the motor 1 to be firmly affixed to housing 5. It will be appreciated that, in many motorized constructions, vibration and audible noise transmitted through the supporting structure can be detected during operation of the transducer drive motor. This is something that causes discomfort for patients and also disturbs the image formation process. Thus, it is desirable to provide the endoscope with a transducer tip housing 5 having a motor damping block (not shown) disposed between the body of motor 1 and support 18. Such a block can be made of an elastomeric material such as silicone rubber (e.g., Alpha Gel from GelTech, Japan) or a polyurethane resin (e.g., PolyBD from Atochem, France), and may be implemented by simply coating or bonding the material directly on the internal, motor receiving surfaces of support 18.

Motor 1 is equipped with a gearbox 12 so as to provide a suitable compromise between the output torque and rotational speed of motor 1. Motors belonging to the group consisting of brushless motors, synchronous motors and magnetic motors can be readily employed for the purposes of the present invention.

A conical output gear 14 of motor 1 is coupled to the transducer gear 21a through torque limitation system or torque limiter 8 disposed at the front of the housing 5. Torque limiter 8 includes a rotatable shaft 24 mounted in a double ball bearing set including an upper ball bearing 28 and lower ball bearing 27. A gear 23 and a clutch wheel 25 are normally engaged together by the pressure exerted by a spring 19 to form a transmission interface with motor 1. Clutch wheel 25 is secured to shaft 24 by a needle screw or set screw 22, while gear 23, which is freely rotatable when not engaged by clutch wheel 25, engages gears 14 of the motor 1. The frictional area 26 located at the interface of gear 23 and clutch wheel 25 is preferably made of a high friction coefficient material having an interface composition such as metal/composite, metal/metal or the like. Alternatively or additionally, the frictional area or interface 26 can also be provided by means of mating surfaces having complementary grooving or other shaping which mate when the mating surfaces are pressed together.

At the top end of the torque limiting assembly 8, axle or shaft 24 terminates in a gear 17 which engages or mates with the transducer gear 21a. It is important to note that gears 21a and 21b are secured to transducer 2 for rotation therewith. Gear 21b is dedicated to an encoding operation and, to this end, engages or mates with an incremental gear 20 in a preferred implementation of the encoding system of the scanhead. The gear ratio of the encoding system is preferably defined by making gear 21b significantly smaller than incremental gear 20 in order to enable the transducer 2 to rotate over 360° while still providing conservation of absolute position encoding.

Figure 3B:
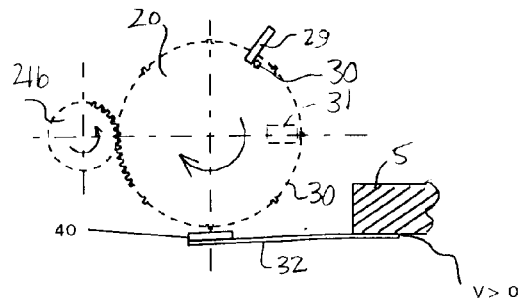

Referring to FIGS. 3a and 3b, which are top plan views, there is shown an encoding gear system according to one preferred embodiment of the invention. For the sake of simplicity, only gears 21b and 20 are represented, together with an abutment 29 and a transducer locking device 32. In normal operation, the gear 20 is designed to rotate through a single turn, and thus a mechanical stop 30 is provided on the surface of gear 20 to physically stop transducer rotation if necessary. In fact, the emergency stop arrangement formed by abutment 29 and stop 30 is only needed when the encoding system fails to detect the corresponding end or final position of motor 1.

In the encoding system of FIGS. 3a and 3b, a position detector 31 is provided which can either be a magnetic detector or a sensor that is sensitive when associated with a magnetic, incrementally patterned disk. Such detectors are conventional and can be bought separately or manufactured as an integrated device such as those available from AustriaMicrosystems of Austria. For example, such a magnetic detector can be a conventional detector which is microfabricated and supplied as a standard IC, or an optical device when a reflective incremental disk is used.

Should encoding system fail to detect the final position of the associated incremental disk (not shown), the transducer 2 will continue to rotate until the abutment 29 is reached and the contact between stop 30 and abutment 29 mechanically stops the transducer rotation. Under the latter circumstances, motor 1 continues to be powered and an overload torque occurs in the torque limiting assembly 8. In order to protect the motor 1, and to protect the scanhead from excessive heating, the clutch system formed by the coupling of gear wheel 25, gear 23 and spring 19 will inhibit development of excessive torque. In this regard, if the torque developed should exceed a predetermined value determined by the frictional force existing at the interface between the gear wheel 25 and gear 23, a slipping or sliding action occurs at this interface to reduce the torque overload on transducer 2 and the heating of motor 1. In addition, an audible noise is produced due to this sliding to alert a user as to the torque overload condition. Additionally, the power supply for motor 1 is automatically shut down if no new incrementing information is supplied to the system after a predefined time period. This additional security positively impacts on the safety of the patient. In this regard, because the internal volume of the scanhead is quite small and the motor 1 is located therein, heat from the motor 1 can rapidly be transferred to the surrounding tissue with a potential risk to the patient. However, if, for the period during which the motor 1 rotates, the resistance torque applied to the motor shaft remains moderate, any heating produced by the Joule effect is minimal and may be neglected.

Returning to the torque limiting assembly 8, the frictional force between gear 23 and gear wheel 25 is set to be slightly higher than that of the resistance torque of the transducer 2. In the case where a geared clutch is used (i.e., that formed by wheel 25 and gear 23) in the torque limiting assembly 8, the profile of the gear teeth of the respective gears and the stiffness of spring 19 are chosen so as to obtain the desired maximum resistance torque. Preferably, very low profile gear teeth are used in order to produce a maximum tangential force when a resistance torque occurs.

It will be understood that gears 14, 17, 23, 21*a* and 21*b* can take other forms and shapes (e.g., straight, conical, or unshaped) and still provide the transmission requirements discussed above. In order to reduce the audible noise produced by mating components, plastic gears with teeth having an exponential profile are preferably used. Further, because the various gears are immersed in the coupling liquid 13, the noise is further reduced.

In a preferred embodiment of the invention, an encoding system is used that detects the absolute angular position of transducer 2 even when the transducer 2 operates in multi-turn rotational mode. The corresponding encoding system can be implemented using various different conventional approaches such as optical, magnetic and the like. During operation, it is desirable to be able to keep the transducer 2 immobile once the desired angular position of transducer 2 is reached.

This action of fixing the position of transducer 2 can be carried out in a manner that is used in conventional systems by supplying a maintaining current to keep the rotor of motor 1 at a fixed angular position. This method has the advantage of being simple to apply. However, maintaining the motor current during the stopping of the transducer 2 will produce electromagnetic interference that may cause white discharges that are visible on the displayed images, i.e., such electromagnetic interference often appears in the displayed image as white discharges or randomly spread white lines.

Because of the disadvantages discussed above, fixing the transducer 2 in position without applying electrical current to motor 1 is desired and, in the embodiment of FIGS. 3*a* and 3*b*, a voltage controlled bimorph actuator 32 is provided as a locking device. As illustrated, the bimorph actuator 32 is of an elongated shape, and is secured at one end to part of the structure of the transducer tip housing 5 and at the opposite end terminates in an elastomeric frictional pad 40. In a standby mode, with no voltage applied to the bimorph actuator 32, actuator 32 is mounted relative to gear 20 in such a manner as to exert pressure against the periphery of gear 20 via the pad 40. The pressure exerted by the bimorph actuator 32 in the standby mode is sufficient to maintain the transducer 2 in position despite any permanent recall torque developed by the flexible PCB 4 on transducer 2. The use of elastomeric frictional pad 40 for stopping the rotation of gear 20 provides an important reduction in the pressure force that must be applied for this purpose, because friction force existing at the contact point will be exponentially expanded with the tangential force applied by the actuator 32.

When rotation of transducer 2 is again desired, an electrical voltage is supplied to the bimorph device 32 as well as to the motor 1, and suitable electrical circuitry (not shown) provides a time delay for the voltage supplied to the motor 1 so that this voltage is delayed sufficiently to allow the bimorph device 32 to disengage pad 40 from the gear 20 and so that an instant thereafter the motor 1 is powered and transducer 2 is caused to rotate. As soon as the transducer 2 reaches its desired position, motor power is cut off and the bimorph 32 device is electrically released so as to, at the same time, lock the transducer 2 in position. Preferably, a piezoelectric bimorph device is used as bimorph device 32 because piezoelectric devices are environmentally insensitive. Further, during standby image acquisition, no electric power is supplied to either motor 1 or the bimorph device 32 so that no electromagnetic interference is produced.

Figure 4A:
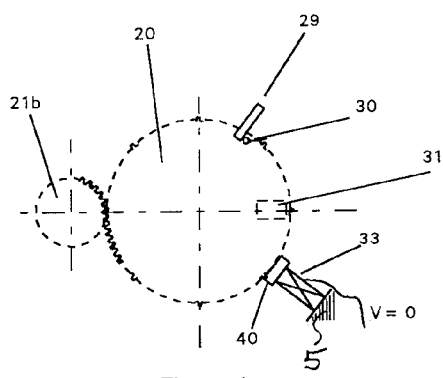
Figure 4B:
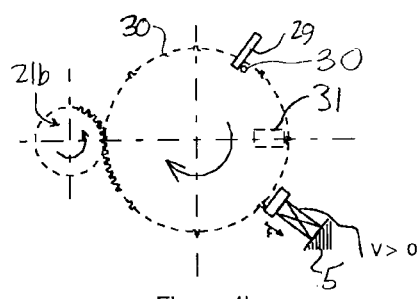

FIGS. 4*a* and 4*b* show another transducer locking system which is also based on the use of frictional force as in the embodiment just described above. The encoding gears 20 and 21*b* are identical, the elastomeric frictional pad 40 provided can be made of the same material without loss of effectiveness. In this embodiment, a longitudinal-acting piezoelectric actuator 33, such as a commercially available piezoelectric actuating device, is used. Preferably, actuator 33 is multilayer device so as to reduce the applied voltage. Parallel amplified actuators can also be utilized as actuator 33. Such actuators are characterized by an external construction that magnifies the displacement of the actuator member. The actuated (locking) and release (unlocking) positions of actuator 33 are shown in FIG. 4*a* and FIG. 4*b*, respectively.

Figure 5A:
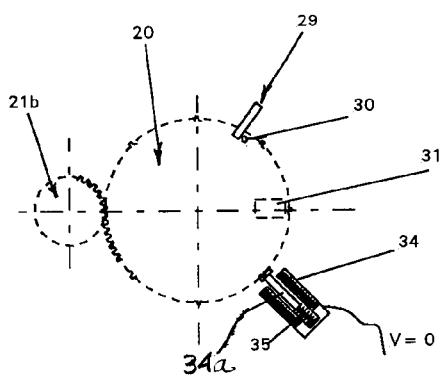
Figure 5B:
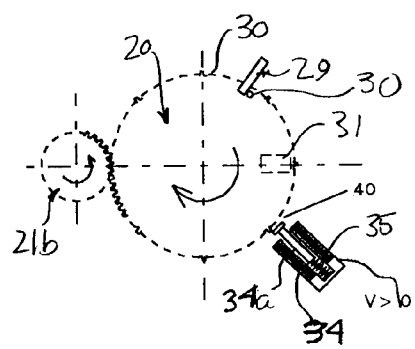

Referring to FIGS. 5*a* and 5*b*, which respectively represent the locked and unlocked position of the gear 20, a pad 40 is also provided to exert a frictional force on gear 20 to fix gear 20 in position. In this embodiment, pad 40 is mounted on the distal end of cylindrical actuator member 34*a* which is actuated by electromagnet 34. The proximal end of actuator member 34*a* is engaged by a compression spring 35 which provides a preloaded force. When a suitable voltage is applied to electromagnet 34, the actuator member 34*a* is pulled inwardly to compress the spring 35, and gear 20 is thus released. Otherwise, the gear 20 is locked.

Referring again to FIG. 2, dedicated openings provided in the membrane 10 allow the electrical connections of transducer tip to extend outwardly from the housing 5 through the membrane 10 to the remainder of the system. Sealing around these connections is preferably carried out using flexible glue (silicone). Although bonding is performed on cables at the membrane interface, the contained liquid 13 can leak through the space separating the wires or the sheath therefor. To avoid this leakage, electrical wires are chosen from among single wire types, and the wire sheath is preferably removed at the passage through the membrane 10 to obtain reliable sealing. On the other hand, because of its construction, no particular special sealing is required for flexible PCB 4.

The procedure for assembly of the motorized endoscopic transducer tip device according to the present invention is generally as follows: sub-components of the transducer tip are assembled into the transducer tip housing 5, and the membrane 10 is then mounted with cables and flexible PCB 4 properly bonded. The transducer tip when so equipped is then immersed in a bath of the coupling liquid 13 under vacuum for a time necessary to degas any air bubbles. The threaded ring 15 is then screwed into place to maintain the membrane 10 in place.

For maintenance and service, as shown in FIG. 2a, a threaded hole 41, sealed by screw 42, is provided at the top face of the transducer tip to enable liquid fill maintenance. However, the liquid filling procedure may be carried out using several other methods without departing from the basic concepts here.

Coupling liquid 13 is preferably chosen from the group consisting of silicon oils, polypropylene glycol, and the like. These liquids exhibit acceptable acoustic properties and lubrication characteristics for the internal transducer mechanism. Compositions of liquid comprising mineral or organic oils can also be employed.

The endoscopic transducer tip according to the preferred embodiments of the present invention described above provides an associated ultrasonic endoscope with unprecedented functionalities, torque limitation and transducer braking. Moreover, the avoidance of seals on the transducer diameter such as are used in conventional devices allows more freedom of transducer motion and enhances acceleration and the rotation rate.

Although the invention has been described above in relation to preferred embodiments thereof, it will be understood by those skilled in the art that variations and modifications can be affected in these preferred embodiments without departing from the scope and spirit of the invention.

What is claimed:

1. An ultrasonic endoscopic probe tip device providing signals to an imaging system for transesophageal diagnosis, said probe tip device comprising:

a removable transducer tip housing adapted to be attached to the distal end of an endoscope;

a mechanical rotating platform supported by said housing;

a rotatable, ball-bearing-mounted phased array transducer supported by said platform, said transducer having an acoustic propagation axis and being rotatable around said axis through multiple turns, and said transducer including an associated drive gear rotatable therewith;

an immersed micro-motorized drive means located adjacent to said transducer;

a torque limiting gearbox coupling said drive means to said transducer;

a position encoder directly mated with the drive gear of the transducer so as to provide the imaging system with transducer position information over a 360° range;

an automatic transducer position locking/unlocking system for locking the transducer in a selected rotational position; and a removable interconnect interface disposed at an interface between the transducer tip housing and a tubular distal end of an endoscopic connection, said interconnect interface comprising electrical interconnections for controlling said transducer drive means as well as said locking/unlocking system and said position encoder.

2. A probe tip device according to claim 1 further comprising a flexible membrane located at the proximal side of the device for containing a filling liquid for the transducer tip housing, said membrane including openings through which pass said electrical interconnections.

3. A probe tip device according to claim 2 wherein the transducer has a footprint of circular shape so as to minimize movement of filling liquid end to enhance transducer acceleration during operation.

4. A probe tip device according to claim 2 further comprising a flexible printed circuit board located beneath the transducer and rotatable therewith, the flexible printed circuit board being sealed at said interconnect interface with said sealing membrane and said housing including room to contain any volume expansion of said printed circuit board produced during coiling thereof.

5. A probe tip device according to claim 4, wherein said flexible printed circuit board has a multi-turn coiled configuration in order to enable the transducer to rotate through more than 360 degrees.

6. A probe tip device according to claim 5 wherein said printed circuit board includes a surface coated with a low friction material to reduce wear at contact areas on the printed circuit board during coiling of the printed circuit board.

7. A probe tip device according to claim 4 wherein the flexible printed circuit board is of a multilayer structure that minimizes printed circuit board height.

8. A probe tip device according to claim 1 wherein said drive means includes a motor and a motor support, and said housing includes damping means disposed between the motor support and the motor so as to minimize mechanical vibrations transmitted to the transducer tip during operation thereof.

9. A probe tip device according to claim 1 wherein the drive means comprises a motor selected from the group consisting of a synchronous motor, a magnetic motor and a brushless motor.

10. A probe tip device according to claim 1 further comprising a torque limiting gear arrangement providing engagement between the drive means and the transducer, said gear arrangement including first and second friction mated, rotating parts, said first part being coupled to the motor and the second part being coupled to the transducer.

11. A probe tip device according to claim 1 wherein said position encoder comprises a disk, including incremental position measurement markings, disposed in mating engagement with the transducer drive gear and a transmitter-receiver sensor device disposed adjacent to said disk for detecting said incremental measurement markings.

12. A probe tip device according to claim 1 wherein said position encoder comprises a disk, including an incremental position measurement pattern, coupled to said transducer drive gear, and optical means for detecting said pattern.

13. A probe tip device according to claim 1 wherein said position encoder comprises a disk having an incremental position measuring magnetic pattern thereon coupled to said transducer drive gear, and a sensor for detecting said magnetic pattern.

* * * * *